United States Patent [19]

Otsuka et al.

[11] Patent Number: 4,910,017

[45] Date of Patent: Mar. 20, 1990

[54] NEW COMPOUNDS WF 2015 A AND B

[75] Inventors: Takanao Otsuka; Toshihiro Shibata; Hiroshi Terano; Yasuhisa Tsurumi; Masakuni Okuhara, all of Tsukuba, Japan

[73] Assignee: Fujisawa Pharmaceutical Company, Ltd., Osaka, Japan

[21] Appl. No.: 261,929

[22] Filed: Oct. 25, 1988

[30] Foreign Application Priority Data

Oct. 26, 1987 [GB] United Kingdom ............... 8725053
Feb. 15, 1988 [GB] United Kingdom ............... 8803428

[51] Int. Cl.$^4$ .................. A61K 35/66; C12N 1/20; C12P 1/02; C12R 1/645
[52] U.S. Cl. ................................ 424/119; 424/120; 435/171; 435/911
[58] Field of Search .................... 424/119, 120, 115; 435/911, 171

[56] References Cited

U.S. PATENT DOCUMENTS 4,512,976  4/1985  Umezawa et al. ............... 424/122
4,530,835  7/1985  Bunge et al. ..................... 424/117
4,554,162  11/1985 Young et al. ..................... 424/117

OTHER PUBLICATIONS

Derwent Abstract 85—174081/29 (J60102190) 6—1985, SS Pharmaceutical.
Derwent Abstract 81—84346D/46 (J56125396) 10—1981, Ajinomoto KK.
Derwent Abstract 81—56232D/31 (J56073096) 6—1981, Shionogi KK.
Derwent Abstract 80—54161C/31 (J55079322) 6—1980, Kyowa Hakko Kogyo KK.

*Primary Examiner*—Herbert J. Lilling
*Attorney, Agent, or Firm*—Oblon, Spivak, McClelland, Maier & Neustadt

[57] ABSTRACT

This invention relates to new compounds WF 2015 A and B which have immunosuppressing activity and antitumor activity, to a process for producing WF 2015 A and B by culturing a WF 2015 A and/or B-producing strain belonging to the genus *Scolecobasidium* in a nutrient medium, and to a pharmaceutical composition comprising the same.

3 Claims, No Drawings

NEW COMPOUNDS WF 2015 A AND B

This invention relates to new compounds WF 2015 A and B. More particularly, it relates to new compounds WF 2015 A and B which have immunosuppressing activity and antitumor activity, to a process for producing WF 2015 A and B by culturing a WF 2015 A and/or B-producing strain belonging to the genus Scolecobasidium in a nutrient medium and to a pharmaceutical composition comprising the same.

The WF 2015 A and B obtained in the Examples as mentioned below have the following physicochemical properties:

(1) WF 2015 A (a) Molecular weight:
410 [FAB-MS: m/z 411 (M+H)]
(b) Elemental analysis:
C 64.55; H 8.06; O 27.39 (by difference)
(c) Optical rotation:
$[\alpha]_D^{23} = -52°$ (C=1.0, CH$_3$OH)
(d) UV absorption spectrum:
End absorption (in CHCl$_3$)
(e) IR absorption spectrum:
$\nu_{max}^{CHCl_3}$: 3450, 2960, 2920, 1710, 1650, 1440, 1370, 1300, 1260, 1200, 1170, 1120, 1100, 1070, 1050, 1000, 980, 920, 880, 830 cm$^{-1}$.
(f) $^1$H NMR absorption spectrum: (CDCl$_3$)

| δ: | 6.95 | (1H, dd, J = 15.5 and 4.5 Hz), |
|---|---|---|
| | 6.20 | (1H, dd, J = 15.5 and 2 Hz), |
| | 5.70 | (1H, broad s), |
| | 5.20 | (1H, broad t, J = 7 Hz), |
| | 4.31 | (1H, m), |
| | 3.90 | (1H, m), |
| | 3.68 | (1H, dd, J = 11 and 3 Hz), |
| | 3.44 | (3H, s), |
| | 2.98 | (1H, d, J = 4.2 Hz), |
| | 2.62 | (1H, dd, J = 6.5 and 6 Hz), |
| | 2.56 | (1H, d, J = 4.2 Hz), |
| | 2.36 | (1H, m), |
| | 2.16 | (1H, m), |
| | 2.10 | (1H, m), |
| | 2.00 | (1H, m), |
| | 1.98 | (1H, d, J = 11 Hz) |
| | 1.87 | (1H, m), |
| | 1.74 | (3H, d, J = 1 Hz), |
| | 1.66 | (3H, d, J = 1 Hz), |
| | 1.21 | (3H, s), |
| | 1.14 | (3H, d, J = 6.5 Hz), |
| | 1.07 | (1H, m) |

(g) $^{13}$C NMR absorption spectrum: (CDCl$_3$)

| δ: | 165.8 | (s), |
|---|---|---|
| | 146.6 | (d), |
| | 135.0 | (s), |
| | 121.8 | (d), |
| | 118.3 | (d), |
| | 79.4 | (d), |
| | 74.5 | (d), |
| | 69.9 | (d), |
| | 66.3 | (d), |
| | 61.1 | (d), |
| | 59.4 | (s), |
| | 58.9 | (s), |
| | 56.7 | (q), |
| | 50.7 | (t), |
| | 48.2 | (d), |
| | 29.2 | (t), |
| | 27.2 | (t), |
| | 25.6 | (q), |
| | 25.6 | (t), |
| | 17.9 | (q), |
| | 17.1 | (q), |
| | 13.7 | (q). |

(h) Solubility:
Soluble: Chloroform, methanol, acetone, ethanol
Insoluble: n-Hexane, water
(i) Color reaction:
Positive: Reaction with iodine vapor
Negative: Ninhydrin reaction, Molish's reaction, ferric chloride reaction,
(j) Property of substance:
Neutral substance

(2) WF 2015 B (a) Molecular weight:
447 [FAB-MS: m/z 469 (M+Na)]
(b) Elemental analysis:
C 58.03; H 7.94; Cl 7.31; O 26.72 (by difference)
(c) Optical rotation:
$[\alpha]_D^{23} -248°$ (C=2.0, CHCl$_3$)
(d) UV absorption spectrum:
End absorption (in CHCl$_3$)
(e) IR absorption spectrum:
$\nu_{max}^{CHCl_3}$ = 3570, 3400, 2960, 2940, 2870, 2820, 1710, 1660, 1560, 1460, 1440, 1400, 1380, 1360, 1340, 1300, 1270, 1220, 1170, 1120, 1080, 1020, 980, 960, 940, 910 cm$^{-1}$.
(f) $^1$H NMR (400 MHz, CDCl$_3$)

| δ: | 6.99 | (1H, dd, J = 5 and 15.5 Hz), |
|---|---|---|
| | 6.20 | (1H, dd, J = 2 and 15.5 Hz), |
| | 5.55 | (1H, m), |
| | 5.18 | (1H, m), |
| | 4.36 | (1H, m), |
| | 3.98 | (1H, dq, J = 4 and 6 Hz), |
| | 3.87 | (1H, d, J = 11 Hz), |
| | 3.49 | (1H, d, J = 11 Hz), |
| | 3.31 | (1H, m), |
| | 3.30 | (3H, s), |
| | 2.97 | (1H, t, J = 6.5 Hz), |
| | 2.50–2.40 | (2H, m), |
| | 2.17 | (1H, m), |
| | 2.05 | (1H, m), |
| | 1.90–1.75 | (2H, m), |
| | 1.73 | (3H, s), |
| | 1.66 | (3H, s), |
| | 1.49 | (3H, s), |
| | 1.40 | (1H, broad d, J = 14 Hz), |
| | 1.20 | (3H, d, J = 6 Hz) |

(g) $^{13}$C NMR (100 MHz, CDCl$_3$)

| δ: | 165.7 | (s), |
|---|---|---|
| | 146.3 | (d), |
| | 134.8 | (s), |
| | 122.4 | (d), |
| | 118.2 | (d), |
| | 78.7 | (d), |
| | 76.2 | (s), |
| | 74.5 | (d), |
| | 70.0 | (d), |
| | 66.1 | (d), |
| | 64.0 | (s), |
| | 62.3 | (d), |
| | 56.7 | (d), |
| | 50.5 | (t), |
| | 43.3 | (d), |
| | 29.1 | (t), |
| | 27.5 | (t), |
| | 25.8 | (q), |
| | 23.5 | (t), |

-continued

| | |
|---|---|
| 22.2 | (q), |
| 17.9 | (q), |
| 17.6 | (q), |

(h) Solubility:
Soluble: Chloroform, methanol, acetone, ethanol
Insoluble: n-Hexane, water
(i) Color reaction:
Positive: Reaction with iodine vapor
Negative: Ninhydrin reaction, Molish's reaction, ferric chloride reaction
(j) Property of substance:
Neutral substance The WF 2015 A and B can be prepared by culturing a WF 2015 A and/or B-producing strain belonging to the genus Scolecobasidium such as *Scolecobasidium arenarium* F-2015 and the like in a nutrient medium and recovering the WF 2015 A and B from the cultured broth. Among a WF 2015 A and/or B-producing strain belonging to the genus Scolecobasidium, *Scolecobasidium arenarium* F-2015 was newly isolated from a decaded wood debris collected at the beach of Uchinada Town, Ishikawa Prefecture, Japan by the present inventors. A lyophilized sample of *Scolecobasidium arenarium* F-2015 was deposited with an International depository authority on Budapest treaty, Fermentation Research Institute, Agency of Industrial Science and Technology, No. 1-3, Higashi 1-chome, Yatabe-machi, Tsukuba-gun, Ibaraki-ken, 305, Japan under the accession number FERM BP-1520 on Oct. 13, 1987.

It is to be understood that the production of the new compounds, WF 2015 A and B are not limited to the use of the particular organism described herein, which is given for illustrative purpose only. This invention also includes the use of any mutants which are capable of producing the WF 2015 A and B including spontaneous mutants as well as artificial mutants which can be produced from the described organism by conventional means, such as X-rays, ultra-violet radiation, treatment with N-methyl-N'-nitro-N-nitrosoguanidine, 2-aminopurine and the like. *Scolecobasidium arenarium* F-2015 has the following morphological, cultural and physiological characteristics.

This organism grew rapidly on various culture media and formed dark olive and felty colonies. During two months, its teleomorph was not observed, while conidial structures were abundantly produced. The conidiogenesis was holoblastic, and conidia were dark, septate and ellipsoidal. The conidiophores were short, simple or branched, and developed in sympodial succession. On the basis of these characteristics, the strain F-2015 appears to belong the hyphomycete genus Scolecobasidium Abbott 1927. Its mycological characteristics were as follows.

Cultural characteristics on various agar media were shown in Table 1. Cultures on corn meal agar grew rapidly, attaining 4.5-5.5 cm in diameter after one week at 25° C. This colony surface was plane, thin, felty and yellowish grey. The reverse was the same. Conidial structures were observed. Colonies on malt extract agar grew in a similar rate on corn meal agar. The surface was plane, felty, sectoring, dark green and olive brown. The reverse was dark green. The conidia were abundantly produced. On malt extract agar with 3.5% NaCl, this strain spread more rapidly than on other media, attaining 8.0 cm in diameter under the same conditions. They were plane, powdery to felty, non-sectoring, and olive to dark olive. The reverse was greenish black. Conidial structures were abundantly formed.

The conidiophores were mononematous, pale brown, smooth, septate, simple or branched, straight or flexuous, (8-)12-35(-70) μm long and 2-4 μm thick. The terminals of each branches were swollen and formed conidia-bearing denticulate portions, measuring 4-5 m in diameter. Sometimes, conidiophores continued growth from the swelling apex and formed a secondary fertile lateral. At the swelling portions, 2 to 12 conidia were produced in clusters. The conidia were brown, obovoid, ellipsoidal to cylindrical, with a marked projection at the base, minutely but distinctly verruculose, 1-3(-5) septate, often with dark septa and a dark spot at both ends, (9-)12-25(-30) μm long and 4-7 μm thick. The vegetative hyphae were septate, hyaline, smooth and branched. The hyphal cells were cylindrical and 2-6 μthick. The chlamydospores were absent.

The strain F-2015 was able to grow at the temperature range from 5 to 37° C. with the growth optimum at 23° to 25° C. These temperatal data were determinated on potato dextrose agar. This strain could grow at pH 4 to 10, and had a growth optimum at pH 6 to 7 in YM broth (Difco). The strain tolerated up to 20% NaCl, while good growth occurred with up to 5% of salinities.

According to the taxonomic criteria of the genus Scolecobasidium, the strain F-2015 resembled *Scolecobasidium arenarium* (Nicot) M. B. Ellis 1976. And above-mentioned characteristics corresponded with this species description by Ellis (Ellis, M. B. More Dematiaceous Hyphomycetes, p. 194, C. M. I. Kew, 1976), without exceptions. Then, we identified the strain as *Scolecobasidium arenarium*, and named it *Scolecobasidium arenarium* F-2015.

TABLE 1

| Cultural characteristics of the strain F-2015. | |
|---|---|
| Medium | Cultural characteristics[1] |
| Czapeck Dox agar | G: Rapidly, 6.5-7.0 cm |
| | S: Olive brown (4F8) |
| | Plane, felty, sectoring |
| | R: Blackish blue (20F4) |
| Corn meal agar | G: Rather rapidly, 4.5-5.5 cm |
| | S: Yellowish grey (3B2) |
| | Plane, thin, felty |
| | R: Yellowish grey (3B2) |
| Malt extract agar | G: Rather rapidly, 4.5-5.0 cm |
| | S: Dark green (30F8), olive brown (4F8) |
| | Plane, felty, sectoring |
| | R: Greenish black |
| Potato dextrose agar | G: Rapidly, 6.0-6.5 cm |
| | S: Olive brown (3F8) |
| | Plane, felty, sectoring |
| | R: Greenish black |
| YpSs agar | G: Rapidly, 6.5-7.0 cm |
| | S: Dark brown (5F5), olive brown (4F5) |
| | Plane, felty to cottony, |
| | R: Bluish grey (20F3) |
| Sabouraud agar | G: Rather rapidly, 5.0-5.5 cm |
| | S: Olive brown (4F5), yellowish brown (5F5) |
| | Plane, felty, sectoring, wrinkly |
| | R: Olivaceous black |
| Oat meal agar | G: Rather rapidly, 5.0-5.5 cm |
| | S: Olive brown (4F4), olive (2F5) |
| | Raised to plane, cottony, sectoring |
| | R: Bluish grey (23F3) |
| MY20 agar | G: Fairly rapidly, 8.0 cm |
| | S: Yellowish brown (5E4), olive (1F4) |
| | Plane, felty |
| | R: Olivaceous black |
| Malt extract agar with 3.5% NaCl | G: Fairly rapidly, 8.0 cm |
| | S: Olive (3F7) |

TABLE 1-continued

Cultural characteristics of the strain F-2015.

| Medium | Cultural characteristics[1] |
| --- | --- |
| | Plane, powdery to felty, R: Greenish black |

(Abbreviation) G: Growth, measuring colony sizes in diameter, S: colony surface, R: reverse.
Note: [1] These characteristics were observed after 7 days of incubation at 25° C. The color descriptions were based on the Methuen Handbook of Colour (A. Kornerup and J.H. Wanscher, Methuen Handbook of Colour, Third ed., Methuen, London, 1983.)

In general, WF 2015 A and B can be produced by culturing a WF 2015 A and/or B producing strain in a nutrient medium containing assimilable sources of carbon and of nitrogen, preferably under aerobic conditions (e.g. shaking culture, submerged culture, etc.).

The preferred sources of carbon in the nutrient medium are carbohydrate such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nutrients, are also suitable for use. When desired, there may be added to medium such mineral salts as calcium carbonate, sodium or potassium phosphate, sodium or potassium iodide, magnesium salt, cobalt chloride and the like. If necessary, especially when the culture medium is formed remarkably, a deforming agent such as liquid paraffin, higher alcohol, plant oil, mineral oil and silicones may be added.

As conditions for the production in massive amounts, submerged aerobic cultural condition is preferred for the production of the WF 2015 A and B. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the WF 2015 A and B. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the WF 2015 A and B.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 25° C., for a period of 50 hours to 100 hours, which may be varied according to the fermentation conditions and scale.

Thus produced WF 2015 A and B can be recovered from the culture medium by conventional means which are commonly used for the recovery of other fermentation products such as antibiotics.

In general, most of the WF 2015 A and B produced are found in the culture filtrate, and accordingly WF 2015 A and B can be isolated from the filtrate, which is obtained by filtering or centrifuging the broth, by a conventional method such as concentration under reduced pressure, lyophilization, extraction with a conventional solvent, pH adjustment, treatment with a conventional resin (e.g. anion or cation exchange resin, non-ionic, adsorption resin), treatment with a conventional adsorbent (e.g. activated charcoal, silicic acid, silica gel, cellulose, alumina), crystallization, recrystallization and the like.

Some biological properties of WF 2015 A and B are illustrated in detail in the following tests.

The WF 2015 A and B can be separated each other and isolated by subjecting a crude material comprising WF 2015 A and B to silica gel column chromatography as exemplified in the Example.

TEST 1 (ANTITUMOR ACTIVITY OF WF 2015 A)

The antitumor activity of WF 2015 A was determined in experimental tumor system in mice.

Mouse fibrosarcoma Meth A was implanted intradermally into Balb/c mice (female, 8 weeks age) at an inoculum size of $1 \times 10^5$ cells per mouse. Twenty-four hours after the implantation of tumor cells, graded doses of WF 2015 A were administered to the mice intravenously. Treatments were once a day on day 1, 2, 3, 4 and 7, 8, 9, 10 after the tumor inoculation. Control animals received intravenous doses of physiological saline solution. The injection volume was 0.2 ml in all experiments. Five mice were used for each experimental group.

Tumor weight at 14 days after administration, as derived from caliper measurements of the length and width of tumors, was calculated by the formula: Tumor weight (mg) $= \frac{1}{2} \times a \times b^2$, where a represents the length and b represents the width (mm).

The results are shown in the following table.

| Dosage of WF 2015 A(mg/kg) | Tumor weight (mg) |
| --- | --- |
| None (Control) | 1136.6 ± 138.3 |
| 10 | 27.7 ± 105.6 |
| 3.3 | 682 ± 131.5 |
| 1.0 | 864 ± 108.7 |

(mean ± S.E., n = 5)

TEST 2 (IN VITRO CYTOTOXICITY OF WF 2015)

Human lung adenocarcinoma A549 cell and mouse lymphoma EL-4 cell were used in this study. A549 cells were propagated as monolayer culture in Dulbecco's medium supplemented with 10% heat inactivated fetal bovine serum (FBS), penicillin G (60 µg/ml) and streptomycin (20 µg/ml) and harvested by trypsinization. EL-4 cells were maintained in RPMI medium supplemented with 10% FBS and the antibiotics in culture flasks.

Exponentially growing cells of A 549 or EL-4, which harvested from the cultures, were suspended in flask in the appropriate medium (Dulbecco's or RPMI medium supplemented with 10% FBS and antibiotics) at a concentration of $2 \times 10^4$ cells/ml or $2 \times 10^5$ cells/ml. respectively. Cells were treated with the graded doses of WF 2015 in plastic tissue culture dishes.

Concentration of the substance required for 50% inhibition of cell growth ($IC_{50}$ value, µg/ml) was determined by plotting the logarithm of the drug concentration versus the growth rate (percentage of control) of the treated cells after 120 hours incubation for A 549 cells and 48 hours incubation for EL-4 cells at 37° C. in humidified atmosphere of 5% carbon dioxide.

The results are shown in the following:

(1) WF 2015 A $IC_{50}$ value: A549 $3.0 \times 10^{-4}$ µg/ml
EL-4 $6.5 \times 10^{-4}$ µg/ml
(2) WF 2015 B $IC_{50}$ value: A549 $1.4 \times 10^{-4}$ µg/ml
EL-4 $5.1 \times 10^{-4}$ µg/ml

TEST 3 (ACUTE TOXICITY OF WF 2015)

Physiological saline solution of WF 2015 A or B (100 mg/kg) was administered to 5 ICR strain mice (female, 5 weeks age) once a day for 5 days, the results are shown that no abnormal symptom of the mice was observed.

TEST 4 [SUPPRESSION OF IN VITRO MIXED LYMPHOCYTE REACTION (MLR)]

The MLR tests were carried out in microtiter plates, with each well containing specified concentration of WF 2015 A and $5 \times 10^5$ C57BL/6 responder cells ($H-2^b$), $5 \times 10^5$ mitomycin C treated (25 µg/ml mitomycin C at 37° C. for 30 minutes) BALB/C stimulator cells ($H-2^d$) in 0.2 ml RPMI 1640 medium, supplemented with 10% fetal calf serum, 2mM glutamine, $3 \times 10^{-5}$M 2-mercaptoethanol, 24 mM sodium bicarbonate, penicillin (50 unit/ml) and streptomycin (50 µ/ml). The cells were incubated at 37° C. in a humidified atmosphere of 5% $CO_2$:95% air for 68 hours and pulsed with $^3$H-thymidine (0.5 µCi) 4 hours before the cells were collected. Radio-activity of the cells was assayed by B-counter. From the resultant data, MLR suppression (%) was calculated. The results are shown in the following table.

| Concentration of WF 2015 A (ng/ml) | MLR suppression (%) |
| --- | --- |
| 10,000 | 94.4% |
| 1,250 | 89.0 |
| 161 | 87.3 |
| 40 | 88.0 |
| 20 | 86.2 |
| 6.6 | 49.1 |
| 0.2 | 9.4 |
| 0.066 | 8.5 |
| 0.02 | 0.4 |
| 0.0066 | 0.0 |

TEST 5 (ANTITUMOR ACTIVITY IN VIVO)

Human MX-1 mammary (each fragment, $3 \times 3 \times 3$ mm), maintained s.c. by serial passage in female BALB/c nu/nu mice aged 6 weeks was implanted s.c. to female BALB/c nu/nu mice on day 0, and WF 2015 A or vehicle were given i.v. to the mice once a day on specified days (day0→4, day 7→11 and day 14→18).

Tumor weight was calculated as follows: (Tumor length and width were measured by caliper.)

Tumor weight $(mg) = \frac{1}{2} \times a \times b^2$, where a represents length and b represents width (mm).

Tumor weights (initial) and (last) were calculated on the first injection day (just before dosing) and on day 21, (the last evaluation day), respectively.

Eight mice were used for each test group and each vehicle-treated control group, respectively.

Drug efficacy was expressed as tumor growth inhibition (%).

The results are shown in the following table.

| Dosage of WF 2015 A (mg/kg) | Tumor Growth Inhibition (%) |
| --- | --- |
| 0(Control) | 0 |
| 10 | 41.2 |
| 30 | 62.6 |

The WF 2015 A and/or B of this invention in admixture with pharmaceutically acceptable carriers can orally or parenterally be administered as immunosupressant or antitumor agent to mammals including human being in a form of a pharmaceutical composition such as capsules, tablets, granules, powders, buccal tablets, sublingual tablets and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. surface active agent, etc.], aqueous diluting agent (e.g. water), oils (e.g. sesame oil, etc.), base wax (e.g. cacao butter, polyethyleneglycol, white petrolatum, etc.).

A dosage of the object compounds are to be varied depending on various factors such as kind of diseases, weight and/or age of a patient, and further the kind of administration route.

The preferred dosage of WF 2015 A or B is usually selected from a dose range of 0.01–10 mg/kg/day in the case of injection and 0.5–50 mg/kg/day in the case of oral administration.

The following Examples are given for the purpose of illustrating this invention.

EXAMPLE 1

An aqueous medium (160 ml) containing 2% of soluble starch, 1% of corn starch, 1% of glucose, 1% of cotton seed flour, 1% of dried yeast, 0.5% of peptone, 0.5% of corn steep liquor and calcium carbonate (pH 6.0) was poured into each of nineteen 500 ml Erlenmeyer flasks and sterilized at 120° C. for 20 minutes. A loopful of slant culture of *Scolecobasidium arenarium* F-2015 was inoculated to each of the medium and cultured under shaking at 25° C. for three days. The resultant culture was inoculated to an aqueous medium (120 l) containing 3% of soluble starch, 1% of glucose, 1% of wheat germ, 0.5% of cotton seed flour and calcium carbonate in 200 l jar-fermenter which had been sterilized at 120° C. for 20 minutes in advance, and cultured at 25° C. for three days.

The cultured broth thus obtained was filtered with an aid of diatomaseous earth (20 kg). The filtrate (95 l) was extracted with ethyl acetate (95 l). This extraction procedure was carried out twice and the extracts were combined. After dehydration with anhydrous magnesium sulfate, the ethyl acetate layer was concentrated in vacuo. The concentrate was applied to a silica gel chromatographic column (1 l). The column was washed with n-hexane (3 l) and a mixture of n-hexane-ethyl acetate (1:1, 3 l). The active fraction was eluted with ethyl acetate (4 l) and then concentrated in vacuo. The elutate was further applied to a silica gel column (400 ml). After washing with chloroform (1.2 l) and a mixture of chloroform-methanol (100:1, 1.2 l), the column was eluted with a mixture of chloroform-methanol (75:1, 50:1 and 25:1) stepwisely. The active fraction was concentrated in vacuo, and the residue was subjected to ODS (YMC) column chromatography. After washing with a mixture of methanol-water (1:1, 300 ml), the columm was developed with a mixture of methanol-water (3:2 and 7:3, 300 ml each) stepwisely. The active fraction was evaporated to dryness under reduced pressure to yield purified colorless oily WF 2015 A (92 mg).

EXAMPLE 2

A loopful of slant culture of *Scolecobasidium arenarium* F-2015 was inoculated into each of sterile seed medium (160 ml) containing 2% of soluble starch, 1% of corn starch, 1% of glucose, 1% of cotton seed flour, 1% of dried yeast, 0.5% of peptone, 0.5% of corn steep liquor, 3% of NaCl and 0.2% of $CaCO_3$ (pH 6.0) poured into each of twenty 500 ml Erlenmeyer flasks, respectively and cultured at 25° C. for 72 hours at 250 rpm using a rotary shaker.

The resultant seed cultured broth was transferred to 160 liters of the same sterile medium in a 200-liter stainless steel fermenter, which was agitated at 200 rpm at 25° C. for 48 hours. Further, 90 liters of thus obtained seed culture was inoculated into 3,000 liters of the production medium containing 3% of soluble starch, 1% of glucose, 0.5% of cotton seed flour, 1% of wheat germ, 3% of NaCl and 0.2% of $CaCO_3$ in a 4,000 liter steel fermenter. The culture was carried out at 25° C. for 72 hours under aeration of 3,000 liters/minutes and agitation of 130 rpm.

The cultured broth (2,850 liters) was filtered with an aid of diatomaseous earth (65 kg). The filtrate was passed through a column of activated carbon (600 liters). The column was washed with 180 liters of deionized water and eluted with 80% aqueous acetone (180 liters). The eluate was concentrated in vacuo to a volume of 17 liters. The concentrate was extracted with 18 liters of ethyl acetate. The ethyl acetate layer was separated and evaporated to dryness to give powder (61.3 g). The crude powder was mixed with 0.3 l of silica gel. The mixture was subjected to a column chromatography using silica gel (3 l). After developing the column with 10 liters of hexane and then 10 liters of hexane-ethyl acetate (1:1), the column was eluted with 10 liters of ethyl acetate. The active fractions were collected and evaporated to dryness to give powder and the powder was mixed with silica gel. The mixture was subjected to a column chromatography using silica gel (1 l). The column was developed with 3 liters of chloroform and then 3 liters of chloroform-methanol (100:1), and eluted with 3 liters of chloroform-methanol (75:1). The eluate was evaporated to dryness to give powder (16.4 g) and the powder was mixed with 30 ml of a reverse phase silica gel ODS. The mixture was subjected to ODS column and developed with 2.4 liters of methanol-water (1:1). The column was eluted with methanol-water (3:2). Active fractions were collected and concentrated under reduced pressure to give WF 2015 B (305 mg).

We claim:

1. New compounds, WF 2015 A and B having the following characteristics:

(1) For WF 2015 A
  (a) Molecular weight:
    410 [FAB-MS: m/z 411 (M+H)]
  (b) Elemental analysis:
    C 64.55; H 8.06; O 27.39 (by difference)
  (c) Optical rotation:
    $[\alpha]_D^{23} = -52°$ (C=1.0, $CH_3OH$)
  (d) UV absorption spectrum:
    End absorption (in $CHCl_3$)
  (e) IR absorption spectrum:
    $\nu_{max}^{CHCl_3}$: 3450, 2960, 2920, 1710, 1650, 1440, 1370, 1300, 1260, 1200, 1170, 1120, 1100, 1070, 1050, 1000, 980, 920, 880, 830 $cm^{-1}$
  (f) $^1H$ NMR absorption spectrum: ($CDCl_3$)

δ: 6.95 (1H, dd, J = 15.5 and 4.5 Hz),
6.20 (1H, dd, J = 15.5 and 2 Hz),
5.70 (1H, broad s),
5.20 (1H, broad t, J = 7 Hz),
4.31 (1H, m)
3.90 (1H, m),
3.68 (1H, dd, J = 11 and 3 Hz),
3.44 (3H, m),
2.98 (1H, d, J = 4.2 Hz),
2.62 (1H, dd, J = 6.5 and 6 Hz),
2.56 (1H, d, J = 4.2 Hz),
2.36 (1H, m),
2.16 (1H, m),
2.10 (1H, m),
2.00 (1H, m),
1.98 (1H, d, J = 11 Hz),
1.87 (1H, m),
1.74 (3H, d, J = 1 Hz),
1.66 (3H, d, J = 1 Hz),
1.21 (3H, s),
1.14 (3H, d, J = 6.5 Hz),
1.07 (1H, m)

(g) $^{13}C$ NMR absorption spectrum: $CDCl_3$)

δ: 165.8 (s),
146.6 (d),
135.0 (s),
121.8 (d),
118.3 (d),
79.4 (d),
74.5 (d),
69.9 (d),
66.3 (d),
61.1 (d),
59.4 (s),
58.9 (s),
56.7 (q),
50.7 (t),

| | |
|---|---|
| 48.2 | (d), |
| 29.2 | (t), |
| 27.2 | (t), |
| 25.6 | (q), |
| 25.6 | (t), |
| 17.9 | (q), |
| 17.1 | (q), |
| 13.7 | (q). |

(h) Solubility:
  Soluble: Chloroform, methanol, acetone, ethanol
  Insoluble: n-Hexane, water
(i) Color reaction:
  Positive: Reaction with iodine vapor
  Negative: Ninhydrin reaction, Molish's reaction, ferric chloride reaction
(j) Property of substance:
  Neutral substance (2) For WF 2015 B:
  (a) Molecular weight:
    447 [FAB-MS: m/z 469 (M+Na)]
  (b) Elemental analysis:
    C 58.03; H 7.94; Cl 7.31; O 26.72 (by difference)
  (c) Optical rotation:
    $[\alpha]_D^{23} -248°$ (C=2.0, CHCl$_3$)
  (d) UV absorption spectrum:
    End absorption (in CHCl$_3$)
  (e) IR absorption spectrum:
    $\nu_{max}^{CHCl_3}$ = 3570, 3400, 2960, 2940, 2870, 2820, 1710, 1660, 1560, 1460, 1440, 1400, 1380, 1360, 1340, 1300, 1270, 1220, 1170, 1120, 1080, 1020, 980, 960, 940, 910 cm$^{-1}$
  (f) $^1$H NMR (400 MHz, CDCl$_3$)

| | |
|---|---|
| δ: 6.99 | (1H, dd, J = 5 and 15.5 Hz), |
| 6.20 | (1H, dd, J = 2 and 15.5 Hz), |
| 5.55 | (1H, m), |
| 5.18 | (1H, m), |
| 4.36 | (1H, m), |
| 3.98 | (1H, dq, J = 4 and 6 Hz), |
| 3.87 | (1H, d, J = 11 Hz), |
| 3.49 | (1H, d, J = 11 Hz), |
| 3.31 | (1H, m), |
| 3.30 | (3H, s), |
| 2.97 | (1H, t, J = 6.5 Hz), |
| 2.50–2.40 | (2H, m), |
| 2.17 | (1H, m), |
| 2.05 | (1H, m), |
| 1.90–1.75 | (2H, m), |
| 1.73 | (3H, s), |
| 1.66 | (3H, s), |
| 1.49 | (3H, s), |
| 1.40 | (1H, broad d, J = 14 Hz), |
| 1.20 | (3H, d, J = 6 Hz) |

(g) $^{13}$C NMR (100 MHz, CDCl$_3$)

| | |
|---|---|
| δ: 165.7 | (s), |
| 146.3 | (d), |
| 134.8 | (s), |
| 122.4 | (d), |
| 118.2 | (d), |
| 78.7 | (d), |
| 76.2 | (s), |
| 74.5 | (d), |
| 70.0 | (d), |
| 66.1 | (d), |
| 64.0 | (s), |
| 62.3 | (d), |
| 56.7 | (d), |
| 50.5 | (t), |
| 43.3 | (d), |
| 29.1 | (t), |
| 27.5 | (t), |
| 25.8 | (q), |
| 23.5 | (t), |
| 22.2 | (q), |
| 17.9 | (q), |
| 17.6 | (q) |

(h) Solubility:
  Soluble: Chloroform, methanol, acetone, ethanol
  Insoluble: n-Hexane, water
(i) Color reaction:
  Positive: Reaction with iodine vapor
  Negative: Ninhydrin reaction, Molish's reaction, ferric chloride reaction
(j) Property of substance:
  Neutral substance.

2. An antitumor pharmaceutical composition comprising, as an effective antitumor ingredient, an effective amount of the WF 2015 A or B of claim 1 and pharmaceutically acceptable carrier(s).

3. An antitumor pharmaceutical composition according to claim 2, wherein WF 2015 A or B is present in an amount of 0.01 to 10 mg/kg/day of a mammal to which it is administered in the case of injection and 0.5 to 50 mg/kg/day of a mammal to which it is administered in the case of oral administration.

* * * * *